United States Patent
Paliwal et al.

(10) Patent No.: US 6,974,254 B2
(45) Date of Patent: Dec. 13, 2005

(54) RADIATION THERAPY VOLUME PHANTOM USING FILM

(75) Inventors: Bhudatt R. Paliwal, Madison, WI (US); Wolfgang Tome, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 184 days.

(21) Appl. No.: 10/171,137

(22) Filed: Jun. 12, 2002

(65) Prior Publication Data

US 2003/0231740 A1 Dec. 18, 2003

(51) Int. Cl.[7] ............ G01D 18/08; H05G 1/60; G03B 42/02
(52) U.S. Cl. ............ 378/207; 378/18; 378/65; 378/167; 378/171
(58) Field of Search ............ 378/18, 65, 167, 378/171, 207

(56) References Cited

U.S. PATENT DOCUMENTS

| | | | | |
|---|---|---|---|---|
| 5,511,107 | A | * 4/1996 | Sliski | 378/207 |
| 6,364,529 | B1 | * 4/2002 | Dawson | 378/207 |
| 6,405,072 | B1 | * 6/2002 | Cosman | 600/426 |
| 6,493,574 | B1 | * 12/2002 | Ehnholm et al. | 600/429 |
| 6,594,336 | B2 | * 7/2003 | Nishizawa et al. | 378/65 |
| 6,675,116 | B1 | * 1/2004 | Ritt | 702/104 |
| 6,712,508 | B2 | * 3/2004 | Nilsson et al. | 378/205 |

FOREIGN PATENT DOCUMENTS

WO        WO 00 29871 A   * 5/2000

OTHER PUBLICATIONS

Paliwal, B. et al.: A spiral phantom for IMRT and tomotherapy treatment delivery verification, Medical Physics, Nov. 2000, AIP for American Assoc. Phys. Med. USA, vol. 27 No. 11, pp. 2503–2507, XP002254903 ISSN 0094–2405 the whole document.*
International Search Report.*
Bhudatt Paliwal, et al., A Spiral Phantom for IMRT and Tomotherapy Treatment Delivery Verification, Med. Phys. 27 (11), pp. 2503–2507, Nov. 2000.

* cited by examiner

*Primary Examiner*—Craig E. Church
*Assistant Examiner*—Allen C. Ho
(74) *Attorney, Agent, or Firm*—Quarles & Brady LLP

(57) ABSTRACT

A volume phantom for radiation therapy verification employs film held in a spiral configuration within a equalizing ring of attenuating material. The ring provides improved uniformity in radiation measurement and may be extended, for example, to a hemisphere to provide improved modeling and simulation of treatments in the region of the head.

20 Claims, 2 Drawing Sheets

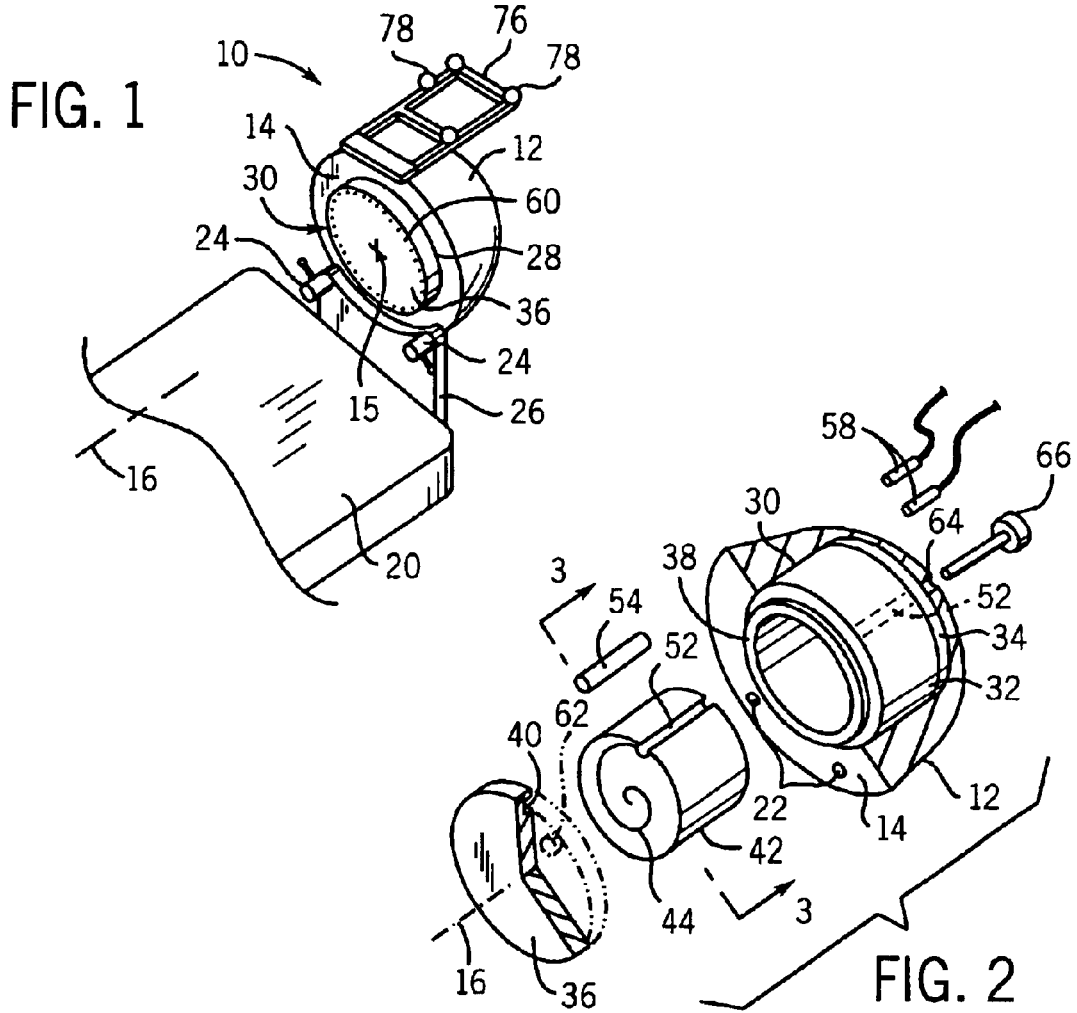
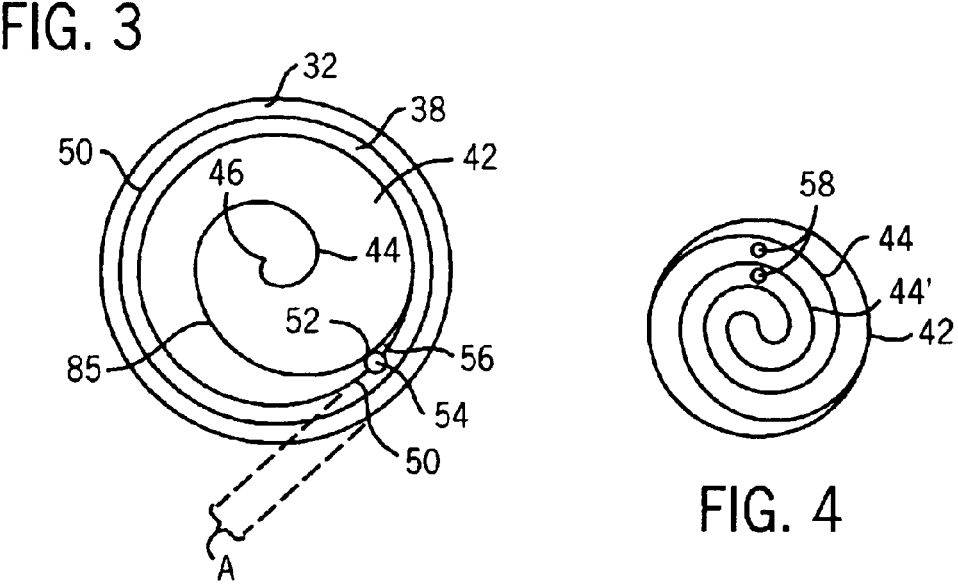

FIG. 5
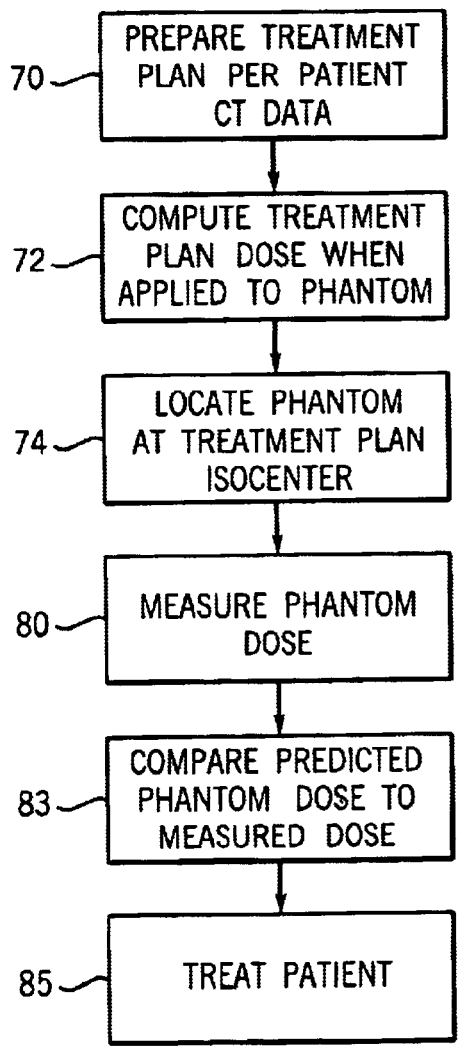
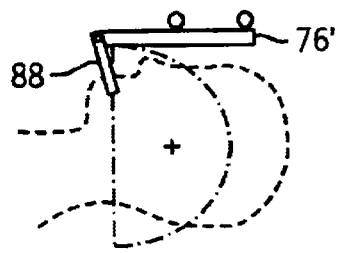
FIG. 6
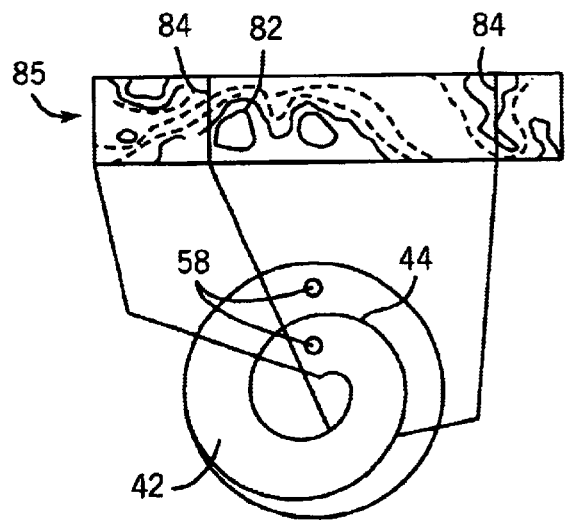
FIG. 7

RADIATION THERAPY VOLUME PHANTOM USING FILM

STATEMENT REGARDING FEDERALLY SPONSORED RESEARCH OR DEVELOPMENT

This invention was made with United States government support awarded by the following agencies: NIH CA14520. The United States has certain rights in this invention.

CROSS-REFERENCE TO RELATED APPLICATIONS

BACKGROUND OF THE INVENTION

This invention relates to the evaluation of radiation therapy phantoms in particular to a phantom using film and providing radiation measurement throughout a volume.

External beam radiation therapy treats cancerous tissue by exposing the tissue to a high-energy radiation from an external source. Normally, a number of different external beams are employed, each approaching the tissue at a different angle, simultaneously or in sequence. The use of multiple beams and angles minimizes the radiation exposure of any given area of the skin and of nearby, possibly radiation-sensitive organs. The selection of the angles and the exposure times for each beam comprises a radiation treatment plan.

Whereas some treatment plans may have a relatively low number of beams and exposure times, the latest generation of radiation therapy equipment allows for extremely complex radiation treatment plans employing many independently controllable beams throughout a range of angles. Multiple beams of varying average intensity may be formed by a multileaf collimator or similar mechanism.

Such complex radiation treatment plans provide precise placement of dose upon tumor tissue, but place severe demands on phantoms used to verify the dose produced by the treatment plan. A conventional radiation therapy phantom incorporates an attenuating material, such as plastic or water, interacting with radiation in a manner equivalent to that of human tissue. One or more radiation detectors, for example, ionization detectors or flat sheets of radiation sensitive film are located within the attenuating material to measure the radiation at different locations.

Conventional phantoms are cumbersome or expensive when accurate characterization of a dose throughout a volume is required, requiring repeated measurements and repositioning of the phantom or its detectors. Accordingly, the present inventors have developed a "spiral" phantom using a single sheet of radiation sensitive film rolled in a spiral to provide dose measurements in a volume rather than a single plane. Knowledge of the mathematical description of the spiral and the properties of the material in which the spiral is cut, allows the radiation measured by the film at different locations upon its two dimensional surface to be related to the doses at different volumes within the three dimensions of the phantom. The spiral phantom is particularly useful for complex intensely modulated radiation therapy protocols and is described in the article: "Spiral Phantom for IMRT and Tomotherapy Treatment Delivery Verification" by Bhudatt Paliwal and Wolfgang Tomé, Susan Richardson and T. Rockwell, Med. Phys. 27(11), November 2000, pp. 2503–2507. These papers are hereby incorporated by reference.

As noted in this paper, although the prototype spiral phantom provided good qualitative assessment of the treatment plan, deviation in the prediction of dose and in the measured dose of the spiral phantom, particularly at the outer arm of the spiral, limited its use in precise quantitative applications.

BRIEF SUMMARY OF THE INVENTION

The inventors have determined that the quantitative accuracy of the spiral phantom may be significantly improved by the addition of a ring of phantom material outside the furthest radial extent of the film. This extra material promotes photon scatter before the radiation strikes the outermost film, providing more uniform sensitivity of the film to radiation over the entire length of the spiral.

The outer ring of phantom material also allows improved clamping and registration of the film, allowing the spiral to be rotated as desired within a fixed outer shell attached to a patient table or the like. The ring may be extended to a hemispherical shell to provide simplified modeling of the expected dose on the phantom and improved simulation for radiation treatment of the head region.

Specifically then, the present invention provides a radiation phantom having a film holder providing a spiral support for radiation sensitive film within an attenuating material. The radiation sensitive film, when placed in the film holder, extends along the spiral support to an outer film limit at which point a housing surrounds the film holder and provides a build up region equalizing radiation sensitivity of the radiation sensitive film near the outer film limit and the radiation sensitive film removed from the outer film limit, i.e., at the center of the spiral.

Thus, it is one object of the invention to provide for greater uniformity in the radiation measurements over the length of the spiral and to improve the quantitative accuracy of the spiral phantom.

The housing may be constructed of a material having radiation attenuation properties similar to those of the material of the spiral support. The materials may mimic the radiation attenuation provided by human tissue.

Thus, it is another object of the invention to provide a uniform phantom that is easily modeled for simulations and that provides a dose distribution similar to that which would be found in a human patient.

The spiral support may be a slot following an Archimedean spiral. The film holder may optionally include a second slot interleaved with the first slot.

Thus, it is another object of the invention to provide for simple structure for supporting the film that similarly provides uniform sampling over a volume. Multiple slots allow arbitrary sampling density to be obtained.

The film holder may be a cylinder and the housing may be a tube fitting around the film holder.

Thus, it is another object of the invention to provide for simple structure allowing preloading of film within the phantom in a protected light-tight configuration.

A clamping means may fit between the cylinder and the housing, pressing the slot about the radiation sensitive film.

It is thus another object of the invention to provide a clamping mechanism for the film. The clamping means may be a wedge inserted between the housing and the film holder and constructed of a material similar to both.

The film holder may include a keying element locking rotation of the film holder with respect to the housing.

Thus, it is another object of the invention to provide positive registration of the film with respect to the housing so that rotation of the housing may be used to accurately position the sampling points of the film within the volume to be measured.

The housing may be a hemispherical outer shell having radiation attenuation properties mimicking human tissue.

It is yet a further object of the invention to provide for a simple phantom shape amenable to simulations and particularly suitable for use in simulations of radiation treatment of the human head.

The foregoing and other objects and advantages of the invention will appear from the following description. In the description, reference is made to the accompanying drawings which form a part hereof and in which there is shown by way of illustration a preferred embodiment of the invention. Such embodiment does not necessary represent the full scope of the invention, however, and reference must be made to the claims herein for interpreting the scope of the invention.

BRIEF DESCRIPTION OF THE DRAWINGS

FIG. 1 is a perspective view of the phantom of the present invention mounted on a patient table showing the attachment of an optical target for alignment of the phantom with an external reference;

FIG. 2 is an exploded, partial cross-sectional view of the components of the phantom of FIG. 1 showing a slotted film holder fitting within an inner tubular housing held by an outer hemispherical outer housing;

FIG. 3 is a cross-sectional view of the film holder and housing of FIG. 2 taken along lines 3—3 of FIG. 2 showing the locking of the film holder and inner housing by means a of cylindrical key and the intermitting of a wedge between the film holder and inner housing to compress the slot about the film;

FIG. 4 is a view similar to FIG. 3 showing the use of two spiral slots to obtain a greater sampling density and showing locations of optional ionization detectors for normalizing the data of the film to quantitative measurements;

FIG. 5 is a flowchart of the steps of using the phantom of the present invention in verifying complex radiation therapy treatment plans;

FIG. 6 is an outline of a patient's head showing the positioning of a bite bar holding an optical target similar to that of the phantom of FIG. 1 (also shown in outline) for alignment of the phantom and patient with the radiation therapy isocenter; and FIG. 7 is a simplified representation of the film exposed in the phantom after processing, such as represents, when flattened, a spiralogram, and showing a mapping of locations on the spiralogram to the volume of the phantom.

DETAILED DESCRIPTION OF THE PREFERRED EMBODIMENT

Referring now to FIG. 1, in a preferred but non-limiting embodiment, the spiral phantom 10 of the present invention includes a hemispherical outer housing 12 having a vertically oriented flat face 14. During use, the flat face 14 may be arranged perpendicularly to a longitudinal axis 16 extending along the length of a patient table 20.

Referring also to FIG. 2, the flat face 14 may include two mounting holes 22 along its lower edge, the mounting holds 22 being threaded to receive turn screws 24. The turn screws 24 may be used attach the flat face 14 to a bracket 26 extending upward from one end of a patient table 20. The bracket 26 is sized so that the hemispherical outer housing 12 is roughly in the same height above the surface of patient table 20 as a patient's head when supported on the surface of patient table 20. The hemispherical outer housing 12 is moved, however, longitudinally beyond the end of the patient table 20 so as not to interfere with a patient location.

The hemispherical outer housing 12 has a cylindrical bore 28 perpendicular to and centered in the flat face 14 to provide a cavity receiving an inner housing 30. The inner housing 30 is cylindrical about an axis of symmetry parallel to longitudinal axis 16 to fit tightly within the cylindrical bore 28.

Referring specifically to FIG. 2, the inner housing 30 is composed of a tubular body 32 having first and second cylindrical end caps 34 and 36 fitting against either end of the tubular body 32 so as to provide an enclosed cylindrical volume therein. The ends of tubular body 32 may include a longitudinally extending circumferential ridge 38 that is received by a corresponding groove 40 in each of the inwardly facing surfaces of end caps 34 and 36. The ridge 38 and groove 40 serve to center the end caps 34 and 36 on the tubular body 32 and to provide a light trap preventing light leakage into the inner volume of the tubular body 32. The end caps 34 and 36 are held to the tubular body by a press fit.

The material of the hemispherical outer housing 12, inner housing 30 and film holder 42 is preferentially selected to mimic human tissue and thus to have a density and atomic number similar to that of water. These materials may be, for example, Lucite or Solid Water, the latter commercially available from Gammex of Middleton, Wis. Preferably, the material of the inner housing 30 is opaque to visible light preventing light exposure problems during the handling of the device.

A cylindrical film holder 42 fits within the volume defined by the tubular body 32 and end caps 34 and 36 and is thus protected from light. The film holder 42 provides a spiral slot 44 extending a full length of the film holder between the cylinder bases. The spiral slot 44 preferably conforms to an Archimedean spiral meaning that its radius from a longitudinal center axis of the cylindrical film holder 42 increases linearly with angle without the center axis of the cylindrical film holder 42. This results in the spiral arms having constant radial separation producing more uniformity of sampling when a detector film is placed within the spiral slot 44. Ideally, this spiral extends at least two revolutions or about 6.6 radians about the axis.

Referring now also to FIG. 3, the spiral slot 44 begins at a center point 46 at the center of the film holder 42 and proceeds outward to an outer film limit 50 being the edge of the film holder 42. At the outer film limit 50, the film 85 is captured by the intermitting of a cylindrical key 54 and a hemicylindrical groove 52 extending axially along the periphery of film holder 42. Deformation of the film 85 between these surfaces, when the cylindrical key 54 is pressed inward by the inner surface of the tubular body 32, holds the film securely.

The key 54 also located the film holder 42 at a predetermined rotational orientation with respect to the tubular body 32 which has a corresponding hemicylindrical groove 52 cut in its inner surface. Further, the inner surface of end cap 36 may include a blind bore 62 receiving an end of the key 54 so as to lock the rotation of the cap 36 to match the orientation of the film 85 held by the key 54. Thus, key 54 locates the beginning of the film 85 with respect to the tubular body 32 and end cap 36.

A wedge 56 may also be fit between the inner surface of the tubular body 32 and the outer surface of the film holder 42 to provide a radial compression to the film holder 42 holding the film 85 securely without movement and with minimal air gaps within the spiral slot 44.

Referring still to FIG. 3, the thickness of the tubular body 32, indicated by dimension A, is sized so as to provide necessary scattering so that radiation striking film 85 within the spiral slot 44 near the outer film limit 50 experiences an exposure per given amount of radiation, similar to the exposure of film 85 near the center point 46 for the same amount of radiation.

It will be understood that the film holder 42 may be preloaded and stored within the inner housing 30 and easily inserted into the hemispherical outer housing 12 as needed so that multiple studies may be readily conducted and time required to load film holder 42 may be avoided. The film 85 may be EDR film from Kodak having a high dynamic range.

Referring to FIG. 4, it will be understood that an arbitrary spatial sampling of a given volume may be achieved by constructing the spiral slot 44 to be of greater or lesser length and thus of a greater or lesser number of turns. Additional sampling can also be obtained, while fixing the slot length and thus retaining the ability to use conventional film sizes, by producing a second spiral slot 44' interleaved with the first. Holes my be bored in the film holder 42 to receive ionization detectors 58 that can provide for quantitative measurements of dose at particular locations within the spiral phantom 10 that may be used to normalize measurements obtained from the film as will be described. The ionization gauges may be inserted into the film holder 42 before placement in the inner housing 30 and appropriate light-tight conduits for the signal wires provided.

Referring again to FIG. 2, the hemispherical outer housing 12 may be sized to contain end cap 36 and tubular body 32 but to expose end cap 36 slightly from the flat face 14 to allow for rotation of the inner housing 30 with respect to the hemispherical outer housing 12. This rotation can bring the spiral slot 44 into a configuration where greater mounts of film cut through a region of interest depending on the particular procedure. The exposed surface of the cap 36 may include angular graduations 60 to be used to control this rotation.

A hole 64 may pass axially through the hemispherical outer housing 12 to the cylindrical bore 28 so as to facilitate the removal of the inner housing 30 using a pusher rod 66 inserted through the axial hole 64 to press against the outer surface of end cap 34.

Referring now to FIG. 5, in use, the phantom 10 may be used to verify a radiation treatment plan developed for a particular patient. As indicated by process block 70, CT data from that patient is to calculate the necessary beams and intensities for a radiation treatment plan according to well-known techniques.

The same radiation treatment plan may then be applied to the phantom 10 of FIG. 1 in a simulation as indicated by process block 72 based on the known materials and geometry of the phantom 10. The hemispherical shape of the phantom 10 makes this simulation process relatively simple and differences between the phantom and the patient are minimized by adopting a simple head-like outer structure and materials that mimic human tissue. Referring to FIG. 7 a mathematical mapping process can relate individual latitude bands 84 crossing the film 85 to similar axial paths through the phantom of the film holder 42. In this way, at process block 72, a simulated film may be created showing exposures of the film per the simulation.

At process block 74, the phantom 10 is located at a treatment isocenter in the radiation therapy machine where the radiation treatment plan is to be effected.

Referring momentarily to FIG. 1, this location of the phantom 10 may be facilitated by the attachment of an optical target 76 to the top of the phantom 10. Such optical targets 76 are well known in the art and make use of triangulation of a series of reflective spheres 78 positioned on the optical target 76 by infrared sensitive scanner camera assemblies (not shown) positioned in a fixed location on the radiation therapy machine. The center 15 of the sphere defining the hemispherical outer housing 12 may thus be located at the isocenter of the radiation treatment plan.

Referring again to FIG. 5, at process block 80, the radiation treatment plan is conducted on the phantom having been preloaded with film. The film is then removed and developed to show on its surface a series of exposure zones 82 having exposure corresponding with radiation received at those zones 82. The actual dose values may be normalized to readings obtained from the ionization detectors 58 with those quantitative measurements interpolated or extrapolated to particular locations on the spiral slot 44.

The measured dose is compared against the expected dose at process block 83. In a first method, the actual film dose maybe compared with the simulated film produced at process block 72 and differences highlighted through a subtraction process indicating differences between the actual and expected doses. Such differences may indicate, for example, improper functioning of a mechanical multileaf collimator of a radiation therapy machine or computational errors in the simulation for radiation treatment planning process. In addition, this comparison process establishes that the proper treatment plan was loaded.

Alternatively or in addition, the data collected from the phantom 10 may be used to construct a three dimensional dose by interpolation to regular Cartesian coordinate points, to be compared against the desired dose map forming the basis for the radiation treatment plan. While generally the dose over the volume of the phantom 10 as used to produce the radiation treatment plan will be slightly different from that computed from the phantom data, the similarities between these doses will be sufficient to allow for a simple quantitative assessment.

When the radiation treatment plan is verified, then at process block 85, the patient may be place in the radiation therapy machine and treated. Referring to FIG. 6, the location of the patient is facilitated by a bite block 88 that may be held within the patient's mouth having attached to it an optical target 76' similar to the optical target 76 used on the phantom 10 thus providing a closed correlation between the phantom data and the patient treatment.

The description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

We claim:

1. A radiation phantom comprising:
    a film holder providing a spiral support for radiation sensitive film within a radiation attenuating material, the radiation sensitive film extending along the spiral support to an outer film limit;
    a housing surrounding the film holder and providing a build up region around the outer film limit equalizing radiation sensitivity of the radiation sensitive film near the outer film limit and the radiation sensitive film removed from the outer film limit; and wherein the housing is constructed of a material having radiation attenuating properties mimicking human tissue.

2. The radiation phantom of claim 1 wherein the housing is constructed of a material having radiation attenuation properties matching those of the spiral support.

3. The radiation phantom of claim 1 wherein the spiral support is an axially extending first slot cut in a material of the film holder, the slot following an Archimedean spiral.

4. The radiation phantom of claim 3 wherein the film holder further includes a second slot interleaved with the first slot.

5. The radiation phantom of claim 1 wherein the film holder is a cylinder and wherein the housing is a tube fitting around the film holder.

6. The radiation phantom of claim 1 further including a hemispherical outer shell having radiation attenuation properties mimicking human tissue and receiving the housing and the film holder therein.

7. The radiation phantom of claim 6 wherein the hemisphere, film holder and housing when assembled together approximate the shape and attenuation of an upper portion of a standard human head.

8. The radiation phantom of claim 6 wherein the hemispherical outer shell includes a mounting means for mounting the hemispherical outer shell to a patient table and further includes an optical alignment target for positioning the hemispherical outer shell with respect to an external reference point.

9. The radiation phantom of claim 7 further including a second optical alignment target having a bite bar adapted to be held within the mount of a patient at a predetermined orientation and position relative to the center of a patient's head equal to the predetermined orientation and position of the optical alignment target of the phantom relative to a center of the phantom.

10. The radiation phantom of claim 6 wherein the housing is rotatably adjustable within the hemispherical outer shell.

11. The radiation phantom of claim 10 including graduations marking rotational movement of the housing within the hemispherical outer shell.

12. The radiation phantom of claim 6 wherein the material of the buildup region and housing are Solid Water.

13. The radiation phantom of claim 1 wherein the housing is a hemispherical outer shell.

14. The radiation phantom of claim 1 wherein the film holder includes a keying element locking it rotationally with respect to the housing.

15. The radiation phantom of claim 1 including a clamping means fitting between the cylinder and the housing to compress the slot about the radiation sensitive film.

16. A method of verifying radiation treatment comprising the steps of:

(1) placing a phantom within the radiation treatment machine, the phantom providing a regular sampling of measurements distributed along a planar spiral in three dimensions through the phantom volume below a housing providing a build-up region equalizing radiation sensitivity of the measurements, wherein the housing and buildup region are constructed of a material having radiation attenuating properties mimicking human tissue;

(2) determining the position of the phantom with respect to the radiation machine;

(3) performing a radiation treatment plan on the phantom and acquiring actual measurements;

(4) simulating the radiation treatment plan on the phantom to determine expected measurements;

(5) comparing the expected measurements to the actual measurements; and (6) only if the comparisons verify the treatment plan, placing the patient at the position of the phantom and performing the radiation treatment plan.

17. The method of claim 16 wherein the treatment plan includes a set of treatment doses including the step of comparing the treatment dose to the actual measurements.

18. The method of claim 16 wherein step (2) is performed using an optical alignment target and including the step of positioning the patient within the radiation treatment machine using a corresponding optical target.

19. The method of claim 16 wherein the comparison provides a set of difference values between actual and expected measurements.

20. The method of claim 16 wherein the phantom includes at least one quantitative radiation detector and including the step of normalizing the actual measurements to a measurement by the quantitative radiation detector.

* * * * *

UNITED STATES PATENT AND TRADEMARK OFFICE
CERTIFICATE OF CORRECTION

PATENT NO. : 6,974,254 B2
DATED : December 13, 2005
INVENTOR(S) : Paliwal et al.

It is certified that error appears in the above-identified patent and that said Letters Patent is hereby corrected as shown below:

Column 3,
Line 33, "intermitting" should be -- interfitting --.

Column 4,
Line 53, "intermitting" should be -- interfitting --.

Column 8,
Line 7, "cylinder" should be -- the film holder --.
Line 8, "slot" should be -- the spiral support --.

Signed and Sealed this

Eleventh Day of April, 2006

JON W. DUDAS
*Director of the United States Patent and Trademark Office*